(12) United States Patent
Mar (10) Patent No.: US 12,208,272 B2
(45) Date of Patent: Jan. 28, 2025

(54) BIOSTIMULATOR HAVING LOCKABLE FIXATION ELEMENT

(71) Applicant: Pacesetter, Inc., Sylmar, CA (US)

(72) Inventor: Craig E. Mar, Fremont, CA (US)

(73) Assignee: PACESETTER, INC., Sylmar, CA (US)

( * ) Notice: Subject to any disclaimer, the term of this patent is extended or adjusted under 35 U.S.C. 154(b) by 87 days.

(21) Appl. No.: 18/095,475

(22) Filed: Jan. 10, 2023

(65) Prior Publication Data

US 2023/0158315 A1    May 25, 2023

Related U.S. Application Data

(63) Continuation of application No. 16/785,172, filed on Feb. 7, 2020, now Pat. No. 11,565,119.

(60) Provisional application No. 62/803,973, filed on Feb. 11, 2019.

(51) Int. Cl.
*A61N 1/37* (2006.01)
*A61N 1/375* (2006.01)
*A61B 17/34* (2006.01)
*A61N 1/362* (2006.01)

(52) U.S. Cl.
CPC ..... *A61N 1/37518* (2017.08); *A61N 1/37512* (2017.08); *A61N 1/3756* (2013.01); *A61B 17/3468* (2013.01); *A61N 1/362* (2013.01)

(58) Field of Classification Search
CPC ............ A61N 1/37518; A61N 1/37512; A61N 1/3756; A61N 1/362; A61B 17/3468
See application file for complete search history.

(56) References Cited

U.S. PATENT DOCUMENTS

| | | | | |
|---|---|---|---|---|
| 5,569,883 A | * | 10/1996 | Walter | A61N 1/056 607/125 |
| 2012/0116489 A1 | * | 5/2012 | Khairkhahan | A61N 1/37518 607/127 |
| 2013/0253532 A1 | | 9/2013 | Fueglister | |
| 2015/0374976 A1 | * | 12/2015 | Régnier | A61N 1/37205 219/121.64 |
| 2019/0083801 A1 | | 3/2019 | Yang et al. | |

* cited by examiner

*Primary Examiner* — Amanda K Hulbert
*Assistant Examiner* — Natasha Patel
(74) *Attorney, Agent, or Firm* — WOMBLE BOND DICKINSON (US) LLP (57) ABSTRACT

A biostimulator, such as a leadless cardiac pacemaker, including a fixation element that can be locked to a helix mount, is described. The fixation element includes a fastener that engages a keeper of the helix mount. When engaged with the keeper, the fastener locks the fixation element to the helix mount. Accordingly, the fixation element does not move relative to the helix mount when the biostimulator is delivered into a target tissue. Other embodiments are also described and claimed.

17 Claims, 4 Drawing Sheets

BIOSTIMULATOR HAVING LOCKABLE FIXATION ELEMENT

This application is a continuation of co-pending U.S. patent application Ser. No. 16/785,172, filed Feb. 7, 2020, which claims the benefit of priority of U.S. Provisional Patent Application No. 62/803,973, filed Feb. 11, 2019, entitled "Biostimulator Having Lockable Fixation Element," and these patent applications are incorporated herein by reference in their entirety to provide continuity of disclosure.

BACKGROUND

Field

The present disclosure relates to biostimulators. More specifically, the present disclosure relates to leadless biostimulators having tissue anchors.

Background Information

Cardiac pacing by an artificial pacemaker provides electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by conventional pacemakers is usually performed by a pulse generator implanted subcutaneously or sub-muscularly in or near a patient's pectoral region. Well known difficulties exist for conventional pacemakers such as complex connectors and/or risks of mechanical failure. As a result, leadless cardiac pacemakers have been developed. Leadless cardiac pacemakers are self-contained and self-sustainable biostimulators that can be attached to tissue within a dynamic environment, e.g., within a chamber of a beating heart. Leadless cardiac pacemakers can deliver pacing pulses directly to a target tissue. Leadless cardiac pacemakers can include tissue anchors that project from a distal end of the pacemaker to engage the target tissue and hold the pacemaker against the tissue after implantation.

SUMMARY

Tissue anchors of leadless pacemakers ensure that a sensing and/or pacing electrode of the leadless pacemaker maintains good electrical contact with the target tissue. For example, a tissue anchor can be a helical metal spring having a sharpened end. The sharpened end can engage the target tissue. A proximal portion of the helical metal spring can be mounted on a body of the pacemaker and provide a spring force to pull the pacing electrode toward and into contact with the target tissue when the helical metal spring is screwed into the target tissue. Such a tissue anchor may not, however, be securely mounted on the body of the leadless pacemaker. For example, the helical metal spring may inadvertently rotate relative to the pacemaker body during tissue engagement or long-term use. When the tissue anchor moves relative to the body, the tissue anchor can disengage from the target tissue and/or the electrode of the leadless pacemaker can lose contact with the target tissue. Existing manners of securing the tissue anchor to the body to prevent such dislodgement, such as adhesives, can degrade over time. Accordingly, leadless cardiac pacemakers can benefit from improvements in securing the tissue anchor to the body of the leadless pacemaker.

A biostimulator, e.g., a leadless cardiac pacemaker, having a fixation element that is securely mounted on a body of the biostimulator is described below. A leadless pacemaker system including the biostimulator and a method of manufacturing the biostimulator are also described. In an embodiment, a biostimulator, such as a leadless cardiac pacemaker, includes a helix mount mounted on a housing (a body of the biostimulator), and a fixation element mounted on the helix mount. The helix mount therefore couples the fixation element to the housing. The helix mount has a mount flange, which provides a helical channel to receive and hold the fixation element. The mount flange includes a keeper to receive a fastener of the fixation element. More particularly, the fastener can be a portion of the fixation element disposed in the keeper.

In an embodiment, the fixation element includes a helix having one or more turns, and the fastener extends between a first turn end of a helix turn and a second turn end of the helix turn. The fastener can extend orthogonal to the helix at the first turn end and the second turn end. More particularly, the fastener can be coupled to the helix at one or more of the first turn end or the second turn end, and can extend through the keeper channel from a portion of the helical channel on a first side of the mount flange to a portion of the helical channel on a second side of the mount flange. The fastener can be a bent portion of the helix, or a stop element that is coupled to the helix by a joint, e.g., a weld. In any case, the fastener can engage the keeper and be rigidly connected to a helical portion of the fixation element such that the keeper interferes with the fastener to resist movement of the fastener and in turn movement of the fixation element relative to the helix mount. Accordingly, the keeper-to-fastener locking mechanism can secure the fixation element to the body of the biostimulator.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Embodiments describe a biostimulator, e.g., a leadless cardiac pacemaker, having a fixation element that is mounted on a housing and includes a helix extending to a leading point for piercing tissue. The biostimulator may be used to pace cardiac tissue. The biostimulator may also be used in other applications, such as deep brain stimulation, and thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator housing. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator includes a fixation element that locks into a helix mount to reduce a likelihood that the fixation element will move relative to the helix mount during use. For example, when a helix of the fixation element is engaged with tissue to fix the biostimulator to a target site, torque applied to the fixation element will not cause the helix to rotate and back away from the tissue into the helix mount. Securing the fixation element to the helix mount can allow for more reliable tissue fixation by reducing a likelihood that the fixation element will rotate relative to the helix mount and/or translate relative to helix mount along a longitudinal axis of the biostimulator. More reliable fixation can reduce variability in tissue scarring around the fixation element because there will be less chance of variable motion of the fixation element. Reduced scarring can promote more consistency in pacing thresholds of the biostimulator. The fixation element described below can also be smaller than other designs, because fewer turns of the helix are required to achieve a secure attachment between the fixation element and the helix mount. In addition to reducing space requirement of the fixation element, assembly of the fixation element to the helix mount can be simplified, since the fastener can securely engage the keeper without using adhesives to bond the fixation element to the helix mount. Accordingly, the lockable fixation element described below provides a compact, easily assembled, and reliable securement between the fixation element and a body of the biostimulator.

Figure 1:
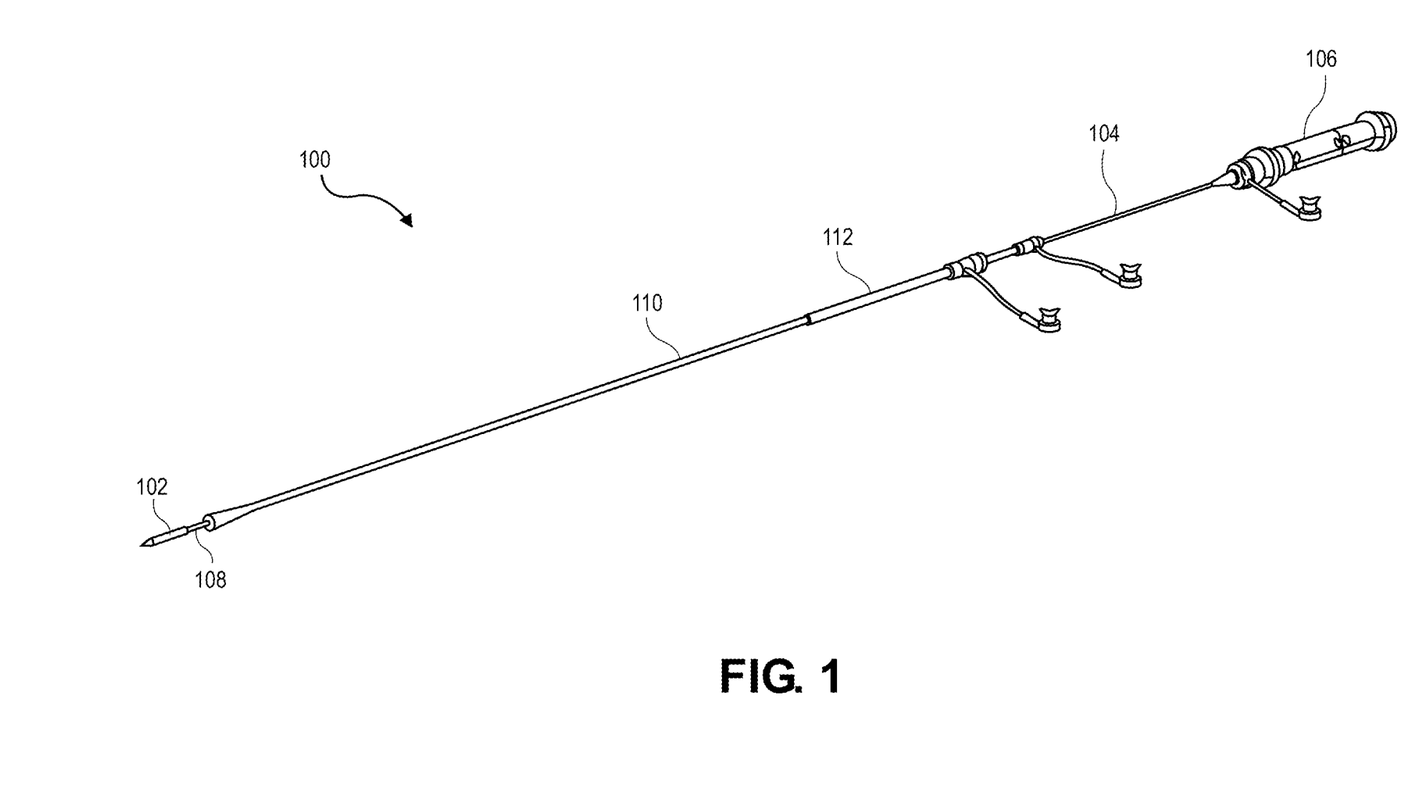
FIG. 1 is a perspective view of a leadless pacemaker system, in accordance with the present disclosure.

Referring to FIG. 1, a perspective view of a leadless pacemaker system is shown in accordance with the present disclosure. A leadless pacemaker system 100 may be used for delivery and/or retrieval of a biostimulator 102, e.g., a leadless cardiac pacemaker, into or from a patient. The leadless pacemaker system 100 can include an elongated catheter 104 extending distally from a handle 106 to a distal end 108. The elongated catheter 104 can be a deflectable catheter, and an operator can use the handle 106 to steer the distal end 108 in the patient. In an embodiment, the leadless pacemaker system 100 includes a guide catheter 110 mounted on the elongated catheter 104. The guide catheter 110 can be slidably disposed on the elongated catheter 104 such that a distal portion of the guide catheter 110 can slide distally over the distal end 108 of the elongated catheter 104 and/or the biostimulator 102. Similarly, the leadless pacemaker system 100 can include an introducer hub assembly 112 mounted on the guide catheter 110. The introducer hub assembly 112 can be slidably disposed on the guide catheter 110 such that a distal portion of the introducer hub assembly 112 can slide distally over the distal end 108 of the elongated catheter 104. More particularly, the introducer hub assembly 112 can be inserted into an access sheath to gain access to the patient vasculature, and after access is established, the distal portion of the guide catheter 110 and/or the distal end 108 of the elongated catheter 104 can be advanced through the access sheath into the patient.

The distal end 108 of the elongated catheter 104 may be selectively connectable to the biostimulator 102. More particularly, the biostimulator 102 can be mounted on the distal end 108 of the elongated catheter 104. The biostimulator 102 can be protected by a protective pacemaker sheath of the distal portion of the guide catheter 110 during delivery and/or retrieval of the biostimulator 102 from the patient. Accordingly, the biostimulator 102 can be advanced into the patient along with the distal end 108.

The leadless pacemaker system 100 can be used to implant one or more biostimulators 102 within an atrium and/or a ventricle of a heart of the patient. Implantation of each biostimulator 102 may be achieved, in part, by endocardial insertion of the biostimulators 102. For example, the elongated catheter 104 of the leadless pacemaker system 100 can be torqueable and can be used to rotate the biostimulator 102. Rotation of the biostimulator 102 when a fixation element (described below) is in contact with the heart tissue can cause the fixation element to screw into the heart tissue and affix the biostimulator 102 to the heart tissue. Similarly, removal and retrieval of the biostimulator(s) 102 may be accomplished endocardially. For example, the torqueable elongated catheter 104 can be rotated to disengage the biostimulator 102 from the heart tissue. Accordingly, delivery and retrieval systems having a structure similar to that shown in FIG. 1 may be used to deliver and/or retrieve biostimulator 102 from a target anatomy.

Figure 2:
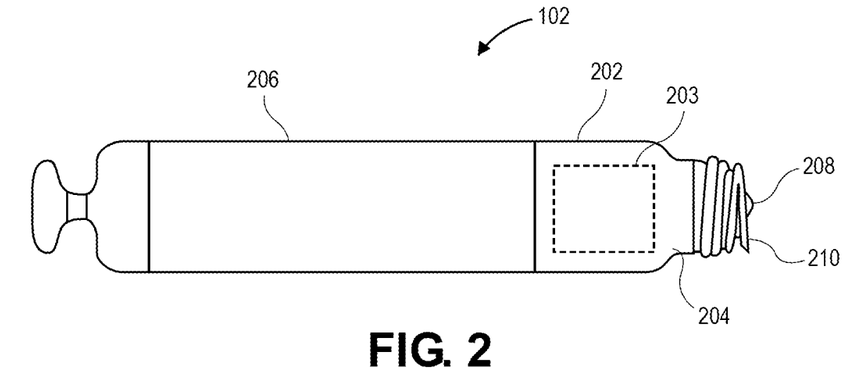
FIG. 2 is a side view of a biostimulator, in accordance with the present disclosure.

Referring to FIG. 2, a side view of a biostimulator is shown in accordance with the present disclosure. The biostimulator 102 can include a housing 202. The housing 202 can be a hermetically-sealed housing, and can include an electronics compartment 203. The electronics compartment 203 may be located within the housing 202, and can contain the electronic components necessary for operation, e.g., sensing and/or pacing, of the biostimulator 102. The hermetic housing 202 can be adapted to be implanted on or in a human heart, and can be cylindrically shaped, rectangular, spherical, or any other appropriate shape. The housing 202 can include a conductive, biocompatible, inert, and anodically safe material such as titanium, 316 L stainless steel, or other similar materials.

The biostimulator 102 can include an insulator 204 disposed on the conductive material of the housing 202 to separate a proximal electrode 206 from a distal electrode 208. The electrodes can include pace/sense electrodes, or return electrodes. A low-polarization coating can be applied to the electrodes, such as platinum, platinum-iridium, iridium, iridium-oxide, titanium-nitride, carbon, or other materials commonly used to reduce polarization effects, for example. In an embodiment, the distal electrode 208 is a pace/sense electrode and the proximal electrode 206 is a return electrode.

In an embodiment, the proximal electrode 206 is integral to the housing 202. Alternatively, the proximal electrode 206 can be connected to the housing 202 at a maximum distance of two centimeters from the housing 202. The distal electrode 208 can also be referred to as a tip electrode, and can be used to sense and/or pace the target tissue when the biostimulator 102 is implanted in the patient. By co-locating the stimulation electrode and the pacing generator of the electronics compartment 203 on the housing 202, and by reducing the pulse generator size to fit within the heart, the biostimulator 102 can be leadless.

The insulator 204 can be an insulating coating on a portion of the housing 202 between the electrodes, and can include materials such as silicone, polyurethane, parylene, or another biocompatible electrical insulator 204 commonly used for implantable medical devices. In the embodiment of FIG. 2, a single insulator 204 is disposed along the portion of the housing 202 between the electrodes. In some embodiments, the housing 202 itself can include an insulator 204 instead of a conductor, such as an alumina ceramic or other similar materials, and the electrodes can be disposed upon the housing 202.

The housing 202 can optionally contain an energy source (not shown) to provide power to the distal electrode 208. The energy source can be a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In an embodiment, the energy source can be an energy harvesting device, such as a piezoelectric device that converts mechanical strain into electrical current or voltage. In certain embodiments, the energy source can be located outside of the housing 202. For example, the energy needed to power the electrical circuits could come from an ultrasound transducer and receiver, which receive ultrasound energy from an ultrasound transmitter located outside of the housing 202.

In an embodiment, the distal electrode 208 is radially inward of a fixation element 210. The fixation element 210 can be a fixation helix or other flexible or rigid structure suitable for attaching the housing 202 to tissue, such as heart tissue.

Figure 3:
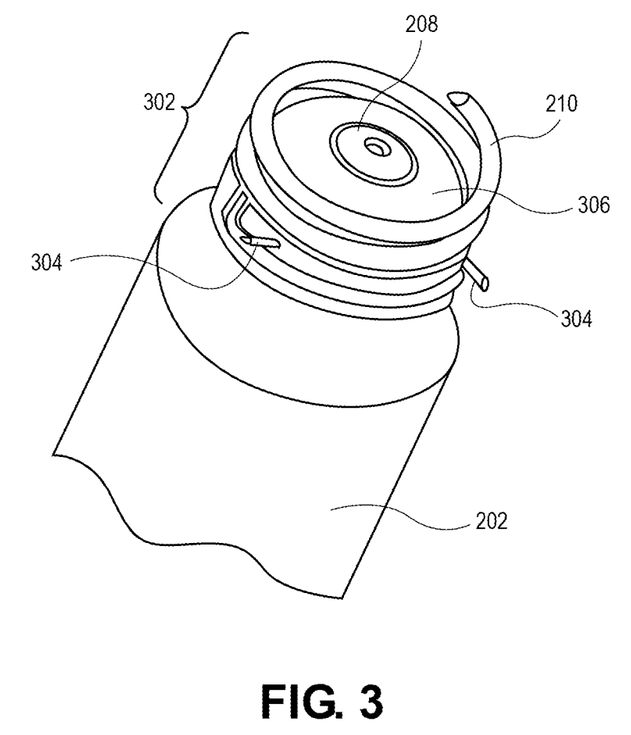
FIG. 3 is a perspective view of a distal portion of a biostimulator, in accordance with the present disclosure.

Referring to FIG. 3, a perspective view of a distal portion of a biostimulator is shown in accordance with the present disclosure. The biostimulator 102 can include a header assembly 302. The header assembly 302 can be mounted on the housing 202 in several ways, including, without limitation, connecting the header assembly 302 to the housing 202 using one or more of a biocompatible adhesive, a threaded connection, or ultrasonic welding.

The header assembly 302 generally includes the fixation element 210 and one or more backstop elements 304. There may be several backstop elements, including forward facing and side facing or laterally extending backstop elements, which provide anti-unscrewing features. More specifically, the fixation element 210 can include a primary helix pointing in a first direction and the backstop elements can include side-facing anti-unscrewing features. The side-facing anti-unscrewing features can include several side-facing sutures extending from an outer surface of the biostimulator 102 in a second direction opposite the first direction. The fixation element 210 may be substantially formed of any suitable biocompatible material including, without limitation, one or more of stainless steel, nickel-titanium alloys (such as Nitinol), nickel-chromium alloys (such as Incoloy®), titanium, and multiphase nickel alloys (such as MP35N® or 35N LT®). The backstop elements may be, by contrast, formed of various flexible biocompatible materials including, without limitation, one or more of polypropylene, polyethylene, polyester, nylon, polyurethane, silicone, poly (lactic acid) (PLA), poly(glycolic acid) (PGA), polyimide, polyether ether ketone (PEEK), and polycarbonate.

The header assembly 302 may include a helix mount 306. The helix mount 306 can couple to and retain the fixation element 210. More particularly, the fixation element 210 can be mounted on the helix mount 306. Similarly, the helix mount 306 can be mounted on the housing 202. Accordingly, the fixation element 210 may be connected to the housing 202 via the helix mount 306.

Figure 4:
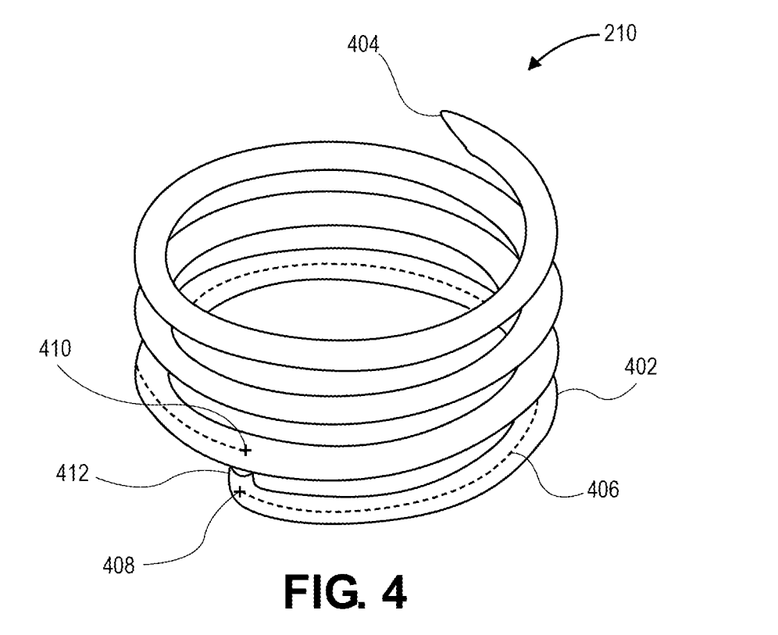
FIG. 4 is a perspective view of a fixation element of a biostimulator, in accordance with the present disclosure.

Referring to FIG. 4, a perspective view of a fixation element of a biostimulator is shown in accordance with the present disclosure. The fixation element 210 can include a helix 402 extending distally from a proximal end to a distal piercing tip 404 over one or more turns 406. Certain dimensions of the fixation element 210 are provided here by way of example and not limitation. The helix 402 can be formed from a wire having wire diameter from and including 0.003 inches to and including 0.03 inches. The wire can be coiled or otherwise formed into a helix corkscrewing about a longitudinal axis. The helix 402 can have a diameter (measured transverse to the longitudinal axis) from and including 0.06 inches to and including 0.3 inches. The helix 402 can have a pitch (measured parallel to the longitudinal axis) from and including 0.01 inches to and including 0.05 inches.

Each turn 406 of the helix 402 can spiral about the longitudinal axis of the fixation element 210 between respective turn ends. For example, a turn 406 of the helix 402 can extend distally from a first turn end 408 to a second turn end 410 over a single revolution of the helix 402. The fixation element 210 can, however, extend over any number of turns 406 from the proximal end to the distal piercing tip 404. For example, in the embodiment illustrated in FIG. 4, the helix 402 continues to extend distally from the second turn end 410 to the distal piercing tip 404 over several, e.g., 2.5, turns or revolutions of the helix 402.

In an embodiment, the fixation element 210 includes a fastener 412 configured to engage a corresponding feature of the helix mount 306. The fastener 412 can be coupled to the fixation element 210 at any location along the fixation element 210. For example, the fastener 412 can be coupled to the helix 402 at the first turn end 408. As described below, the fastener 412 can be integral to the helix 402, e.g., may be a bent segment of the fixation element 210, or may be an additional component, e.g., may be a wire segment, bonded to the helix 402.

Figure 5:
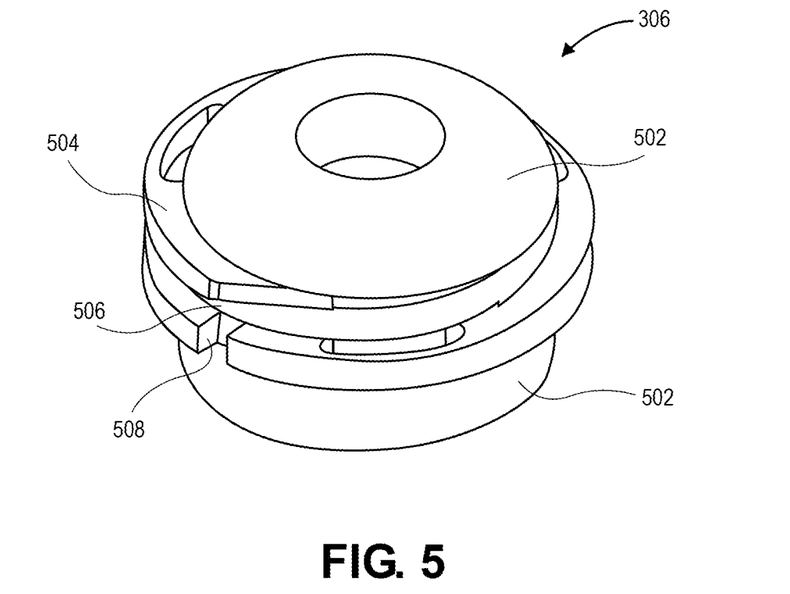
FIG. 5 is a perspective view of a helix mount, in accordance with the present disclosure.

Referring to FIG. 5, a perspective view of a helix mount is shown in accordance with the present disclosure. The helix mount 306 can include a mount body 502, which can be a central portion of the helix mount 306 that mounts on the housing 202 of the biostimulator 102. The helix mount 306 can have a cylindrical outer surface facing radially outward from the longitudinal axis, and an interior cavity having a cylindrical inner surface facing radially inward from the longitudinal axis. Accordingly, the helix mount 306 can have an annular wall extending along the longitudinal axis. In an embodiment, the mount body 502 can have an internal thread formed in the inner surface within the interior cavity. The internal thread can engage an external thread on the housing 202 such that the helix mount 306 can be screwed onto a distal end of the housing 202.

The mount body 502 can have a semi-closed end. For example, the mount body 502 can include a distal cap at a distal end of the helix mount 306. The distal cap can span in a transverse direction across the longitudinal axis to enclose a distal end of the interior cavity of the mount body 502. Thus, a distal surface of the distal cap can face substantially longitudinally, and a proximal surface of the distal cap can face the interior cavity. The distal cap can be a bulbous portion at a distal end of the helix mount 306 that has a smooth and curved, atraumatic, outer surface. The distal cap can be a semi-closed end of the mount body 502 because a central hole may be formed through the distal cap along the longitudinal axis. The central hole can receive the electrode tip (as shown in FIG. 3). The electrode tip can project distally from the mount body 502 to engage tissue when the fixation element 210 is screwed into the target site.

In an embodiment, the helix mount 306 includes a mount flange 504. The mount flange 504 can extend radially outward from the mount body 502. For example, the mount flange 504 can spiral around an outer surface of the mount body 502 in a threaded fashion from a distal end of the mount flange 504 to a proximal end of the mount flange 504. The threaded mount flange 504 spirals around the mount body 502 to form a helical channel 506 between the flange walls. The helical channel 506 can be a helical groove shaped to receive the helix 402 of the fixation element 210. For example, the helix 402 can be screwed onto the mount flange 504 to secure the fixation element 210 to the helix mount 306 and the housing 202. Accordingly, the mount flange 504 provides a holding thread to receive and hold the fixation element 210.

The helix mount 306 can have a keeper 508 in the flange walls. The keeper 508 can be configured to receive the fastener 412 of the fixation element 210 to lock the fixation element 210 to the helix mount 306. More particularly, the fastener 412 of the fixation element 210 can be inserted into the keeper 508 of the helix mount 306 to lock the components together, and the fastener 412 can be removed from the keeper 508 to unlock the components.

Figure 6:
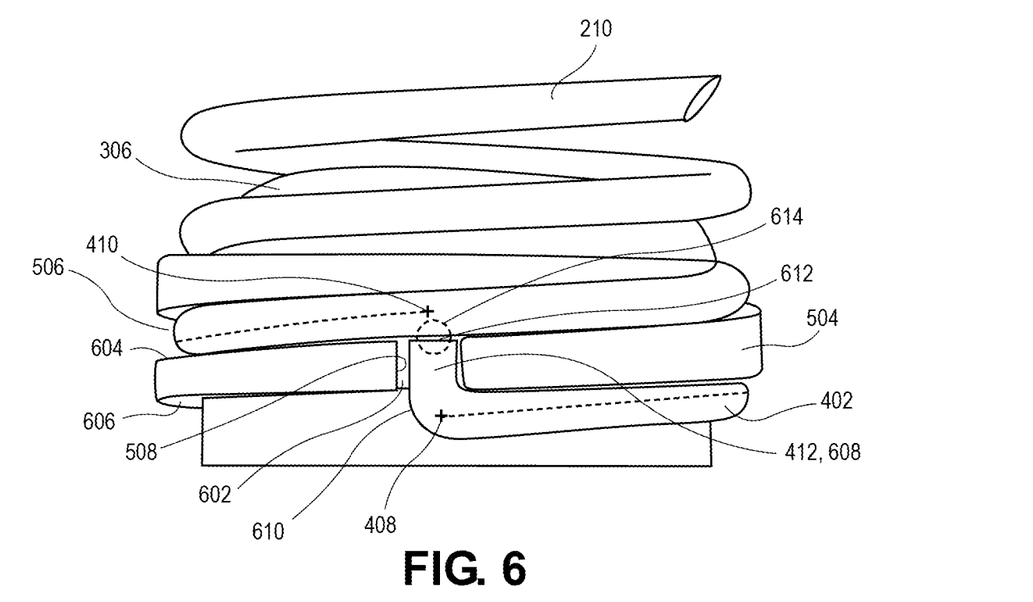
FIG. 6 is a side view of a fastener of a fixation element engaged with a keeper of a helix mount, in accordance with the present disclosure.

Referring to FIG. 6, a side view of a fastener of a fixation element engaged with a keeper of a helix mount is shown in accordance with the present disclosure. The keeper 508 in the mount flange 504 can include an axial channel 602 extending through the mount flange 504. For example, the axial channel 602 can be a slot, a cut-out, a pocket, a recess, or another void formed in the threaded body of the mount flange 504 such that an opening is created in the threaded body between a first side 604 of the mount flange 504 and a second side 606 of the mount flange 504. Whereas the axial channel 602 can extend axially through the mount flange 504, the helical channel 506 extends on both the first side 604 and the second side 606 of the threaded body of the mount flange 504. Accordingly, the axial channel 602 intersects the helical channel 506 on the first side 604 and the second side 606 of the mount flange 504.

The axial channel 602 of the keeper 508 connects a portion of the helical channel 506 on the first side 604 of the mount flange 504 to a portion of the helical channel 506 on the second side 606 of the mount flange 504. The axial channel 602 can be substantially axial, such that a point within the portion of the helical channel 506 on the first side 604 of the mount flange 504 is longitudinally separated from a point within the portion of the helical channel 506 on the second side 606 of the mount flange 504. The points in the helical channel 506 coincide with the turn ends 408, 410 of the helix 402 when the fixation element 210 is located within the helical channel 506. The points represent ends of the turn 406 of the helical channel 506, and coincide with the first turn end 408 and the second turn end 410 of the helix 402. Accordingly, the keeper 508 extends through the mount flange 504 between turn ends 408, 410 of the helical channel 506.

In an embodiment, when the fixation element 210 is threaded onto the mount flange 504 of the helix mount 306, the fastener 412 is disposed in the keeper 508. The fastener 412 can extend into the keeper 508 from the helix 402. The fastener 412 can extend substantially axially between the points on either side of the mount flange 504. Accordingly, the fastener 412 is disposed in the keeper 508 between the first turn end 408 and the second turn end 410 of the helix 402.

Given that the fastener 412 can extend through the keeper 508 in a substantially axial direction, and the helix 402 extends on either side of the mount flange 504 in a spiral or transverse direction, the fastener 412 can be orthogonal to the helix 402 at one or more of the first turn end 408 or the second turn end 410. For example, the fastener 412 can extend orthogonal to the helix 402 at both the first turn end 408 and the second turn end 410. Orthogonality between the fastener 412 and the helix 402 can create a stop feature that engages the keeper 508 when torque is applied to the helix 402. For example, a leftward torque applied to the fixation element 210 of FIG. 6 may cause the fastener 412 to press against a left face of the keeper 508. By contrast, a rightward torque applied to the fixation element 210 of FIG. 6 may cause the fastener 412 to press against a right face of the keeper 508. In both cases, the keeper 508 can interfere with the fastener 412 and resist motion of the fastener 412, and thus, can prevent rotation of the fixation element 210 relative to the helix mount 306. In other words, the pocket in the mount flange 504 acts as a stop in either rotational direction. Since the helix 402 cannot rotate when the fastener 412 is engaged with the keeper 508, a likelihood that the fixation element 210 can move translationally (forward or backward relative to the housing 202 or the target tissue along a longitudinal axis of the biostimulator 102) is reduced.

In an embodiment, the fastener 412 is integral to the helix 402. The fastener 412 can be a segment 608 of the fixation element 210, which extends from the helix 402. The segment 608 can extend from a proximal end of the helix 402. For example, the first turn end 408 may be a proximal end of the helix 402, and the fixation element 210 may be bent at the first turn end 408. Accordingly, the segment 608 can be the bent portion of the fixation element 210 that extends from a bend 610 at the first turn end 408. The bend 610 can be a 90° bend of the fixation element 210 wire at the first turn end 408. The segment 608 can extend into the keeper 508 from the bend 610 toward the helix 402 on an opposite side of the mount flange 504. More particularly, the segment 608 can extend from the bend 610 to a segment end 612 distal from the first turn end 408.

The segment end 612 of the fastener 412 can be a free end, or the segment end 612 can be fastened to one or more of the mount flange 504 or the helix 402. The fastener 412 can extend toward the helix 402 on an opposite side of the mount flange 504 such that the fixation element 210 self-intersects across the keeper 508.

In an embodiment, the segment end 612 is coupled to the helix 402 at a location distal from the keeper 508. For example, the segment end 612 can be coupled to the helix 402 at the second turn end 410, which is longitudinally separated from the bend 610. The fastener 412 can be coupled to the helix 402 by a joint 614. The joint 614 can be, for example, a thermal or adhesive bond. In an embodiment, the joint 614 is a weld that affixes the segment end 612 to the helix 402 at the second turn end 410.

Figure 7:
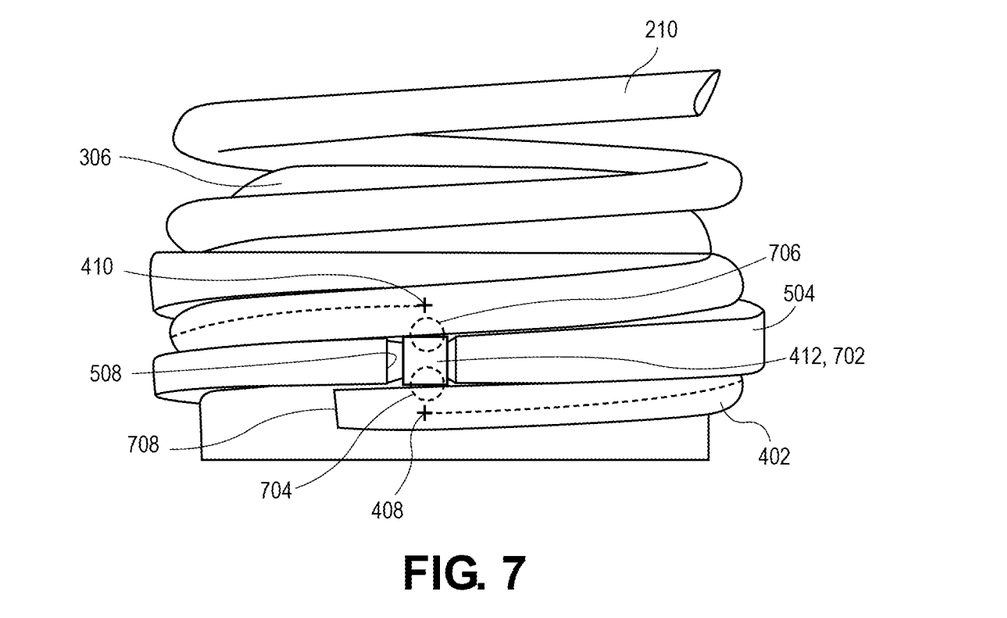
FIG. 7 is a side view of a fastener of a fixation element engaged with a keeper of a helix mount, in accordance with the present disclosure.

Referring to FIG. 7, a side view of a fastener of a fixation element engaged with a keeper of a helix mount is shown in accordance with the present disclosure. In an embodiment, the fastener 412 is a stop element 702, which is a separate component than the helix 402. The fastener 412 can be coupled to the helix 402 at one or more of the first turn end 408 and/or the second turn end 410. For example, as described above, an integral fastener 412 can be coupled to the helix 402 at the first turn end 408 by the bend 610, and the fastener 412 can be coupled to the helix 402 at a second turn end 410 by the joint 614. Similarly, the stop element 702 can be coupled to the helix 402 at the first turn end 408 by a first joint 704, and the fastener 412 can be coupled to the helix 402 at the second turn end 410 by a second joint 706. The joints 704, 706 can be, for example, thermal or adhesive bonds. In an embodiment, the joints 614 704, 706 are welds that affix the stop element 702 to the helix 402 at the turn ends 408, 410.

One or more of the first joint 704 or the second joint 706 are optional joints. More particularly, the stop element 702, which may be a short segment of wire or another piece of material that fits within the keeper 508, can be joined to the helix 402 on only one side of the mount flange 504. In an embodiment, the stop element 702 is joined to the helix 402 at the first turn end 408 and extends distally into the keeper 508 to a free end near the second turn end 410. In another embodiment, the stop element 702 is joined to the helix 402 at the second turn end 410 and extends proximally into the keeper 508 to a free end near the first turn end 408. Optionally, the stop element 702 is joined to the helix 402 at both turn ends 408, 410. As described above, the keeper 508 can resist movement of the stop element 702 when torque is applied to the fixation element 210. Accordingly, when the fastener 412 is engaged with the keeper 508, a likelihood of relative movement between the fixation element 210 and the helix mount 306 is reduced.

The fastener 412 can extend from the helix 402 at a location that is at or distal to a proximal end 708 of the fixation element 210. As shown in FIG. 7, the joint 614 between the stop element 702 and the helix 402 is at the first turn end 408 distal to (in a helical direction along the helix 402) the proximal end 708 of the helix 402. By contrast, as shown in FIG. 6, the bend 610 between the segment end 612 and the helix 402 is at the first turn end 408, which is coincident with the proximal end 708 of the fixation element 210. One skilled in the art can contemplate other configurations, however, in which the fastener 412 is integral to the helix 402 and is distal from the proximal end 708 of the fixation element 210. For example, the fastener 412 can be a U-shaped bend that extends distally into the keeper 508 from the bend 610 at the first turn end 408 and then extends proximally out of the keeper 508 to a second bend (not shown). The fastener 412 can transition into the helix 402 at the second bend to run proximally around the mount body 502. Such a configuration can allow for the fastener 412 to be positioned at any turn of the mount flange 504. For example, although the fixation element 210 has been represented with only a single fastener 412 near the proximal end 708 of the helix 402 in the illustrations, the fixation element 210 may include several fasteners 412 extending through respective keepers 508 at different locations along the mount flange 504. Accordingly, the biostimulator 102 can have several fastener-keeper locking pairs to secure the fixation element 210 and reduce a likelihood of relative movement between the fixation element 210 and the helix mount 306.

Having described the structure of the fixation element 210 and the helix mount 306 of the biostimulator 102, it shall be apparent that a method of assembly may be used to lock the fixation element 210 to the helix mount 306. In an embodiment, the helix mount 306 can be mounted on the housing 202. For example, an internal thread of the mount body 502 can be engaged with an external thread of the housing 202, and the helix mount 306 can be screwed onto the housing 202. At an operation, the fixation element 210 can be mounted on the helix mount 306. The helix 402 of the fixation element 210 can be screwed into the helical channel 506 defined by the mount flange 504. While threading the fixation element 210 onto the mount flange 504, the fastener 412 can ride over a radially outward surface of the mount flange 504. More particularly, the mount flange 504 can resiliently deflect a portion of the fixation element 210 (having the fastener 412) radially outward while the fastener 412 slides over the mount flange 504 toward the keeper 508. At an operation, the fastener 412 can be engaged into the keeper 508. When the fastener 412 slides over the mount flange 504 to the location of the keeper 508, a spring force of the deflected fixation element 210 can resiliently deflect the fastener 412 radially inward into the keeper 508. The fastener 412 can therefore be locked into the keeper 508 between the first turn end 408 and the second turn end 410 of the helix 402, and further rotation of the fixation element 210 can be resisted by contact between an inner wall of the keeper 508 and an outer surface of the fastener 412.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator, comprising:
   a housing containing an electronics compartment;
   a helix mount mounted on the housing and including a mount flange having a holding thread forming a helical channel; and
   a fixation element mounted on the helix mount, wherein the fixation element includes a helix extending about a longitudinal axis and having a first turn and a second turn in the helical channel, and a joint connecting the first turn to the second turn, wherein the holding thread is longitudinally between the first turn and the second turn to interfere with the fixation element and resist motion of the joint relative to the helix mount when a torque is applied to the fixation element.

2. The biostimulator of claim 1, wherein the helix mount includes a mount body, and wherein the mount flange spirals around the mount body to form the helical channel.

3. The biostimulator of claim 1, wherein the joint includes a weld between the first turn and the second turn.

4. The biostimulator of claim 3, wherein the weld is between a first turn end of the first turn and a second turn end of the second turn.

5. The biostimulator of claim 1, wherein the joint connects the first turn to the second turn through a void formed in the mount flange.

6. The biostimulator of claim 5, wherein the void connects a first portion of the helical channel on a first side of the mount flange to a second portion of the helical channel on a second side of the mount flange.

7. The biostimulator of claim 6, wherein the first portion is longitudinally separated from the second portion.

8. The biostimulator of claim 1, wherein the biostimulator is a leadless cardiac pacemaker.

9. A leadless pacemaker system, comprising:
an elongated catheter having a distal end; and
a leadless cardiac pacemaker mounted on the distal end, wherein the leadless cardiac pacemaker includes
a housing containing an electronics compartment,
a helix mount mounted on the housing and including a mount flange having a holding thread forming a helical channel, and
a fixation element mounted on the helix mount, wherein the fixation element includes a helix extending about a longitudinal axis and having a first turn and a second turn in the helical channel, and a joint connecting the first turn to the second turn, wherein the holding thread is longitudinally between the first turn and the second turn to interfere with the fixation element and resist motion of the joint relative to the helix mount when a torque is applied to the fixation element.

10. The leadless pacemaker system of claim 9, wherein the helix mount includes a mount body, and wherein the mount flange spirals around the mount body to form the helical channel.

11. The leadless pacemaker system of claim 9, wherein the joint includes a weld between the first turn and the second turn.

12. The leadless pacemaker system of claim 11, wherein the weld is between a first turn end of the first turn and a second turn end of the second turn.

13. The leadless pacemaker system of claim 9, wherein the joint connects the first turn to the second turn through a void formed in the mount flange.

14. The leadless pacemaker system of claim 13, wherein the void connects a first portion of the helical channel on a first side of the mount flange to a second portion of the helical channel on a second side of the mount flange.

15. The leadless pacemaker system of claim 14, wherein the first portion is longitudinally separated from the second portion.

16. A method, comprising:
mounting a helix mount on a housing containing an electronics compartment, wherein the helix mount includes a mount flange having a holding thread forming a helical channel;
mounting a fixation element on the helix mount, wherein the fixation element includes a helix extending about a longitudinal axis and having a first turn and a second turn in the helical channel; and
forming a joint connecting the first turn to the second turn proximal to the mount flange, wherein the holding thread is longitudinally between the first turn and the second turn to interfere with the fixation element and resist motion of the joint relative to the helix mount when a torque is applied to the fixation element.

17. The method of claim 16, wherein the joint includes a weld between the first turn and the second turn.

* * * * *